(12) United States Patent
Korpela

(10) Patent No.: US 8,771,551 B2
(45) Date of Patent: Jul. 8, 2014

(54) METHOD OF TREATING WOOD

(75) Inventor: Antti Korpela, Espoo (FI)

(73) Assignee: Metsäliitto Osuuskunta, Metsa (FI)

( * ) Notice: Subject to any disclaimer, the term of this patent is extended or adjusted under 35 U.S.C. 154(b) by 661 days.

(21) Appl. No.: 12/478,909

(22) Filed: Jun. 5, 2009

(65) Prior Publication Data

US 2009/0304939 A1 Dec. 10, 2009

(30) Foreign Application Priority Data

Jun. 6, 2008 (FI) .................................... 20085564

(51) Int. Cl.
*A01N 3/00* (2006.01)
*A01N 25/04* (2006.01)
*B27K 3/38* (2006.01)
*B27K 3/34* (2006.01)

(52) U.S. Cl.
CPC . *A01N 3/00* (2013.01); *A01N 25/04* (2013.01); *B27K 3/38* (2013.01); *B27K 3/34* (2013.01)
USPC ...................................................... 252/380

(58) Field of Classification Search
CPC ........... A01N 3/00; A01N 25/04; B27K 3/34; B27K 3/38
USPC ...................................................... 252/380
See application file for complete search history.

(56) References Cited

U.S. PATENT DOCUMENTS

| | | | |
|---|---|---|---|
| 4,919,724 A | | 4/1990 | Cenisio et al. |
| 5,163,931 A | * | 11/1992 | Aldrett ........................... 604/374 |
| 5,447,689 A | * | 9/1995 | Gibboni et al. ................ 422/408 |
| 5,472,485 A | * | 12/1995 | Pandian et al. ............. 106/203.3 |
| 5,484,509 A | * | 1/1996 | Famili et al. ................... 162/135 |
| 5,885,340 A | * | 3/1999 | Bailey et al. ................ 106/209.1 |
| 6,123,760 A | * | 9/2000 | Varnell ....................... 106/174.1 |
| 6,183,550 B1 | * | 2/2001 | Conner et al. .............. 106/209.1 |
| 7,078,454 B2 | * | 7/2006 | Burleigh et al. ............... 524/507 |
| 7,270,727 B2 | * | 9/2007 | Varnell ....................... 162/164.6 |
| 7,317,053 B1 | * | 1/2008 | Gelman et al. ................. 525/178 |
| 7,429,309 B2 | * | 9/2008 | Propst et al. ................ 162/168.1 |
| 2002/0100566 A1 | * | 8/2002 | Lee et al. ....................... 162/166 |
| 2005/0222309 A1 | * | 10/2005 | Bauer et al. .................... 524/115 |
| 2006/0292951 A1 | * | 12/2006 | Dutkiewicz et al. ............ 442/79 |
| 2009/0186162 A1 | * | 7/2009 | Namba et al. .................. 427/511 |
| 2010/0248334 A1 | * | 9/2010 | McDaniel .................. 435/262.5 |
| 2010/0297460 A1 | * | 11/2010 | Kukkonen et al. ......... 428/537.1 |

FOREIGN PATENT DOCUMENTS

| | | | | |
|---|---|---|---|---|
| EP | 1716995 A2 | 11/2006 | | |
| FI | 96626 B | 4/1996 | | |
| FI | 20031103 A | 1/2005 | | |
| FI | 20070935 A | * 12/2007 | ................ | 428/537.1 |
| SU | 532525 A1 | 10/1976 | | |
| WO | 2005/009700 A1 | 2/2005 | | |
| WO | WO 2005/009700 A1 | 2/2005 | | |

OTHER PUBLICATIONS

Finish Search Report for Finish Patent Application No. 20085564 dated Mar. 23, 2009.
Williams, R. Sam & Feist, William C., "Water Repellants and Water-Repellant Preservatives for Wood", United States Department of Agriculture, Forest Service, Forest Products Laboratory, pp. 1-12, Jan. 1999, Madison, WI.
Onoda, K., "Chemical Modification of Wood", Mokuzai Koguo vol. 44, No. 511, pp. 476-480 (1990)—English Abstract.

* cited by examiner

*Primary Examiner* — Gregory Webb
(74) *Attorney, Agent, or Firm* — McCormick, Paulding & Huber LLP

(57) ABSTRACT

A method of protecting wood. According to the method, an aqueous dispersion of alkyl ketene dimer is applied onto the surface of the wood. By means of this treatment, the surface becomes hydrophobic and the contact angle of water in the form of drops on the treated wooden surface exceeds 100°. Such drop-shaped water does not penetrate into the treated surface, nor into for instance a crosscut end of sawn timber. Instead, the water disappears from the surfaces by evaporation.

20 Claims, No Drawings

METHOD OF TREATING WOOD

CROSS REFERENCE TO RELATED APPLICATION

Applicant hereby claims foreign priority benefits under U.S.C. §119 from Finnish Patent Application No. 20085564 filed on Jun. 6, 2008, the contents of which are incorporated by reference herein.

FIELD OF THE INVENTION

The present invention relates to a method of treating wood, such as sawn lumber, laminated structures—typically veneer based products, such as plywood, laminated-veneer-lumber (LVL)—and other wood-based products.

The present invention also relates to wood-based products, which are treated with a wood protection agent in order to improve its hydrophobicity.

BACKGROUND OF THE INVENTION

Wood protection agents are available for improving the water repellency of wood, which agents typically comprise 10-20% binder such as resin or varnish, a solvent such as petrol, mineral oil, alcohol or water, and wax which generates water repellency. Often the wood protection agents also comprise agents which prevent microbiological growth, such as growth of mould. The purpose of the binders is to adsorb the compounds which generate water repellency, as well as other potential protection agents, onto the surface of the wood. Another purpose of the binders is to mechanically close the pores of the wood.

Disadvantages of the currently used compounds described above, which improve the water repellency, are their high price and the organic solvents, found in several products, which are harmful to people and to the environment. Other weaknesses are a long drying time of the binders and, among other things, the susceptibility of varnish to spontaneous combustion. Furthermore, many current treatments impair the breathability of the surface, impairing the drying of the product. The conventional substances leave a waxy layer on the surface which makes the product slippery.

SUMMARY OF THE INVENTION

It is an aim of the present invention to eliminate at least a part of the disadvantages associated with the known solutions and to provide a completely new solution for improving the water repellency of wood.

The present invention is based on the finding that the tendency of wood to absorb water can be reduced by applying an aqueous dispersion of alkyl ketene dimer (hereinafter AKD) onto the surface of the wood material. This dispersion is applied onto an unmodified or untreated wooden surface. For example, the surface of lumber which has not been protected against moisture and fungi is such a surface. Also untreated plywood or LVL is generally classified as "unmodified". After the application of AKD, the water is vaporized. In order to enhance the treatment, it is possible and in some instances even advantageous to carry out the vaporization at an elevated temperature.

By using the present invention, a wood-based product is achieved, on the surface of which an aqueous dispersion of AKD is applied. This wood-based product comprises wood as such or for example a laminated structure where the wood component of the product conventionally would readily absorb moisture and water.

In a preferred embodiment, the protection agents comprise surface-sizing agents which are used in the paper industry. Hence, the present invention provides a new use of an agent conventionally designated for surface-sizing of paper. In particular, the invention provides the use of a surface-sizing agent which comprises or consists of a dispersion of AKD as a wood protecting agent.

More specifically, the method according to the present invention is mainly characterized by what is stated in the characterization part of claim 1.

The product according to the present invention is, in turn, characterized by what is stated in the characterization part of claim 13, and the use according to the present invention is characterized by what is stated in claim 15.

Considerable advantages are achieved with the present invention. Thus, by means of the invention it is possible to significantly improve the water repellency of wood-based products. Such products include sawn wood, such as sawn lumber, and laminated wood or vaneer-based products, such as plywood manufactured from softwood or hardwood, particle boards, chipboards, fibre boards, oriented strand boards and various composite boards, as well as laminated veneer lumber (LVL) products and similar glue-laminated lumber and oriented strand lumber products. As a result, the usability of the wood-based product in conditions where the woody component thereof is exposed to liquid water is significantly improved. Along with improved water repellency, the dimensional stability, the strength and the microbiological resistance of the wood-based product are improved, too.

Another significant improvement is that the weight of the wood-based product which does not absorb water does not increase after it has been exposed to water. Here "water" means liquid water, such as rain water or tap water. The treatment does not significantly affect the migration of gaseous water into the wood or evaporation of it from the wood. Consequently, the present treatment leaves the surface of the wood steam-permeable, i.e. breathable.

The present treatment is more affordable than earlier solutions, is free of organic solvents and non-toxic to people and environment. In addition, the treatment is very effective and generates a strong hydrophobicity on the surface: the contact angle of water which is in the form of drops on the treated wooden surface is over 100°. Typically, drops of water do not penetrate into treated surfaces, not even into a crosscut end of sawn timber. Instead, it evaporates from the surfaces. It should be noted that the absorption of water into an untreated surface always depends on the quality of that surface, and it takes place within a few minutes or even in a few seconds.

Summarizing it can be pointed out that the present treatment reduces swelling of wood products significantly; it gives better dimensional stability which results in enhanced assembly tolerances and better quality of the structures. It keeps the products dry, which stands for shorter drying periods before closing the structures and, consequently, faster building time and energy savings. Naturally, the lower moisture content of the wood products means that for the treated products there is a lower risk of mold growth or blue stain during storing as well as a low risk of damages caused by wet structures.

In addition, no negative effects have been found on strength properties, in reaction to fire or fire resistance, durability of the product, corrosion of metal fasteners, environmental friendliness or health & safety properties.

DETAILED DESCRIPTION OF THE PREFERRED EMBODIMENTS

In the following, the present invention will be examined more closely with the aid of a detailed description.

As mentioned above, in the present context, "wood-based product" stands for different sawn goods, such as unplaned and planed sawn timber, beaded-surface wood, sized laminated timber, sized laminated board, pressure impregnated wood, plywood products, chipboard, fibre board, laminated veneer lumber and products made of these materials, such as furniture and structures.

"Alkyl ketene dimers", i.e. AKD:s, are additives which are used in hydrophobing paper and cardboard. The AKD:s comprise a lactone ring, to which two hydrocarbon chains are attached by means of chemical bonds, the carbon chain length of which varies typically between $C_6$-$C_{39}$. Typically, the carbon chains are straight-chained and saturated, but there are also commercial products in which the carbon chain is branched and/or unsaturated. The hydrocarbon groups of AKD comprise especially approximately 6-30 carbon atoms, in which case particularly common are those which comprise 12-20 carbon atoms. Typical hydrocarbon groups are the hexadecyl and/or octadecyl groups.

Conventional surface-sizing agent compositions are also called alkyl ketene dimer waxes.

In PCT patent application PCT/FI2004/000462, a method of treating wood that has previously been heat-treated is described, in which method the wood is impregnated with a surface-sizing agent, such as AKD or ASA, which is dissolved in an organic solvent. According to the publication, the heat treatment per se improves the resistance of wood to decay, but at the same time the heat-treated wood easily absorbs large quantities of water when it comes into contact with water or damp soil. Thus, the aim of the known solution is to reduce the penetration of water into the wood, because this penetration significantly increases the weight of the wood. An organic solvent is used to enhance the impregnation of the wood. In the PCT publication there is a note about using a surface-sizing agent without any solvent, but no reference to fresh wood or otherwise untreated or unmodified wood (for instance dried sawn timber or untreated laminated wood products) being successfully protected with an aqueous dispersion of AKD.

In the method according to the present invention it has been unexpectedly discovered that it is possible to apply an aqueous dispersion of AKD onto the surface of unmodified or untreated fresh/dried wood-based products, in which case the result is, following the vaporization of the water, a significant improvement in the hydrophobicity of the surface, and, as a result, the resistance of the product to decay is improved. The aqueous dispersion can be applied onto the surface of the woody component either by brushing or by spraying the dispersion onto the surface of the wood. Roller spreading is also possible.

Impregnation (in particular pressure impregnation) is not needed; on the contrary, in a particularly preferred embodiment, the AKD is applied onto the surface in such a fashion that it does not form an integral film layer covering the whole surface of the product. As a result, water repellency in combination with breathability is achieved. The surface is not slippery either.

It is obvious that no other possible means of applying the AKD dispersion is excluded. Thus, as an alternative, it is also possible to pour the dispersion on the surface of the wood, or the wooden surface can be dipped into that dispersion. However, according to the present invention, a good result is achieved simply by spreading the aqueous dispersion on the surface of the wood ("surface application").

The concentration of the AKD dispersion used in the present invention is at least 0.1%, preferably exceeds 0.2%, and at maximum 10%, preferably the dispersion contains approximately 0.5-3% AKD and especially approximately 1.5-2.5%. The percentages are calculated based on the total weight of the dispersion. Because AKD is used as an aqueous dispersion, higher concentrations of the treating agent are possible than for instance when AKD is dissolved in acetone.

The concentration depends on the absorption capacity of the wood to be treated, i.e. the quantity of dispersion which is absorbed by the wood during the treatment.

A typical quantity that is absorbed when applying by brushing, spraying or even dipping (quick dip) is 1 liter per 3-10 $m^2$ of wooden surface. In practice, this means that approximately 0.5 to 30, or 1 to 30 g of AKD is applied/$m^2$ of the surface of the wood product. Amounts from about 0.5 up to 10 g of AKD/$m^2$ are usually sufficient.

Thus, the amount of AKD (expressed in the form of pure hydrophobic agent (="wax") applied onto the surface of the product can be for example about 0.5 to 6.5 g/$m^2$ and the concentration of the AKD dispersion used can be adjusted depending on the actual product to be treated and depending on how much AKD dispersion is absorbed by the product.

When, for example, plywood is treated, it typically absorbs about 70 to 130 ml/$m^2$ of the AKD dispersion and when the concentration of the AKD in the dispersion is about 2% by weight, the applied amount of AKD is about 1.4 to 2.6 g/$m^2$. It appears, somewhat surprisingly, that when the amount of AKD varies within this range, the exact amount does not have a decisive impact on the hydrophobing action As mentioned above in passing, according to one embodiment, the AKD applied onto the surface of the wood product does not form an integral film thereon, but rather separate, discrete spots, which preferably are evenly distributed over the surface. This embodiment allows for effecting breathing of the treated surface. The term "breathing" is herein used to designate the phenomenon of "adsorption and desorption" of gases and liquids.

A new and unexpected observation is that the AKD dispersion, which in the treatment of paper and cardboard products performs best in neutral conditions (AKD size is also known as "neutral size"), works well when the surface of the wood is at a natural, unadjusted pH level, which pH on a moistened surface, for instance for pine and spruce, varies between 3.5-5.5.

Accordingly, the method does not require adjustment of the pH of the wooden surface. In the method according o the present invention, AKD does not essentially comprise any other compounds than AKD, water and an agent which is used for improving the stability of the AKD dispersion, which agent can be for instance starch (for instance cationic starch). The amount of the agent which improves the stability is typically approximately 0.01-20 weight-%, especially approximately 0.1-10 weight-% of the dispersion.

It is obvious that it is possible to add into the dispersion compounds which improve the microbiological resistance of the wood or add other functional compounds, i.e. active compounds. Examples of these are colouring agents and agents which improve the resistance to the effects of light. It should be noted that light color (dye/pigments) can also be added for traceability.

Examples of compounds and agents which improve the microbiological resistance of the wood are iodine-2-propynyl-butyl carbamate, 2-(tiocyano-methylthio)benzothiazole used either alone or in conjunction with methylenebis(thiocyanate), zinc naftenate, copper naftenate, copper-8-quinolinoleate, a mixture of bis(tributyl tin) and N-trichloromethyl-thiophtalimide, and pentachlorophenole and its derivatives. It is also possible to use different materials which chelate metals, such as amino-carboxylates and amino-carboxylic acids, for instance EDTA and NTA.

The quantities of the above mentioned active additives are typically approximately 0.01-10 weight-%, especially approximately 0.1-5 weight-% of the dispersion.

The treatment according to the present invention affects neither the colour nor the odour of the wood. The treatment is complete when the water has been evaporated, although an elevated temperature for instance in the range of 60-130° C. improves the performance of the treatment. The longer the treatment the more effective it is, particularly when the drying is carried out at a relatively low temperature (<60° C.).

The solution, according to the present invention, which improves the water repellency of the wood, is very affordable, as is demonstrated by the following calculations: the price of commercial AKD dispersion, the concentration of which is 20% when delivered is, according to the price level at the filing date, € 700/1000 liters, i.e. € 0.70/liter. The price of AKD which is diluted to a concentration of 2% is € 0.07/liter, provided that the price of the water is not taken into account. Assuming that one liter is enough to treat a wooden surface of 5 $m^2$, the chemical cost of the treatment of one square meter is € 0.014 (€ 1.4/100 $m^2$).

The very low price and the ease of application together make it possible to waterproof for instance sawn timber used in building sites, sawn timber used for transport pallets, and other relatively low-priced sawn timber.

Experts obviously know that it is possible to combine the present treatment with drying of sawn timber. Similarly, it is possible to incorporate the present treatment into the production line of the manufacture of plywood, laminated vaneer lumber and other wood products, in which a plurality of layers are glued together and to carry out the treatment both on-line and off-line. On-line application can be effected on a surface which already is warm (as a result of the previous processing step) or which is heated in a following treatment step. This will promote drying of the dispersion applied to the surface by enhancing evaporation of the aqueous phase. Off-line means that the products is treated only after the last conventional manufacturing step. The treatment can in this case be carried before drying or after drying of the product.

For the purpose of the present invention, the terms "untreated" or "unmodified" will be used with respect to the wood product. These terms designate wood products in which the wood component previously, i.e. in an earlier treatment step, has not been chemically treated to increase the water repellency (="untreated") or it has not been physically modified by, e.g. heat treatment, to achieve the same end (="unmodified"). Not only fresh wood is covered but also dried wood-based products since the latter will exhibit a considerable tendency to absorb water. If there is a prior layer on the surface, it may be planed or sanded off.

According to one embodiment, in a method of protecting wood a hydrophobing agent is applied onto the surface of the wood in order to improve the water repellency of the wood, whereby the hydrophobing agent used is an aqueous dispersion of alkyl ketene dimer, which is applied onto the surface of untreated wood.

According to another embodiment of the invention, a wood product is achieved, on the surface of which an aqueous dispersion of AKD is applied, where the amount of AKD exceeds 0.2 weight-% and at maximum 10 weight-%. This wood product comprises wood which has not been not protected previously by any other treatment, such as heat treatment, against the harmful effects of micro-organisms.

According to a preferred embodiment, the initial stage of protecting wood against the harmful effects of micro organisms is carried out by using the present method. Typically, these microorganisms are rot fungi (such as white rot fungi and brown rot fungi) and fungi which cause a blue stain. Accordingly, it is possible to apply an aqueous dispersion of alkyl ketene dimer onto untreated wood in order to protect this wood during a period of outdoor storage or for instance to protect wood structures during the time of construction. However, it should be noted that the effect of the treatment is only slowly reduced over time because the material is not significantly washed off the wood after the drying of the dispersion; also the resistance of the material to the effects of light is good, too.

The present invention also comprises treating laminated structures, such as plywood and LVL products with AKD applied in the form of an aqueous dispersion. The amount of AKD applied to the surface of the plywood or LVL product is about 0.5 to 6.5 g/$m^2$.

Thus, according to a further preferred embodiment, the present invention provides a plywood or veneer based product, such as LVL, having at least one surface coated with 0.5 to 6.5 g/$m^2$ of AKD.

Because the method is highly efficient, is environmentally friendly and, among other things, because it is odourless and colourless, it is suitable also for the treatment of wood products which undergo a very high degree of processing.

The following non-limiting examples illustrate the present invention:

Example 1

An aqueous dispersion of AKD having a concentration of 2% was brushed onto the surface of planed spruce board. The aqueous dispersion was prepared by diluting a conventional surface-sizing agent composition (Hydrores 350 M, deliverer Kemira Oyj) with water. The amount of water absorbed was approximately 0.2 liters/$m^2$. The spruce boards were dried in a ventilated oven at a temperature of 90° C. for a period of 60 minutes. The water repellency of the spruce board was studied by dropping drops of water onto its surface, including the surface of the crosscut end. The board which was treated with AKD did not absorb any drops of water at all. The contact angle of the water is over 110° C. The untreated reference board absorbed the drops of water within a period of 60-120 seconds. The surface of the crosscut end of the spruce board absorbed the drops in only 3-10 seconds.

Example 2

An aqueous dispersion of AKD which was prepared in the same way as in example 1 and which had a concentration of 2% was brushed onto the surface of planed spruce board. The spruce boards were dried at room temperature for a period of 12 hours. The water repellency of the spruce board was studied by dropping drops of water onto its surface, including the crosscut end surface. The drops of water were slowly absorbed into the board treated with AKD in such a manner that after approximately five hours some of the drops were partly absorbed into the wood. The contact angle of the water is less than in example 1, but still over 90°. The untreated reference board absorbed the drops of water within a period of 60-120 seconds. The crosscut end surface absorbed the drops in only 3-10 seconds.

Example 3

An aqueous dispersion of AKD having a concentration of 2% was sprayed onto the surface of chipboard (see Examples 1 and 2) by means of a manual spray. The amount of the absorbed dispersion was approximately 0.05 liters/m$^2$. The chipboard was dried in a ventilated oven at a temperature of 110° C. for a period of 30 minutes. The contact angle of the water was 100-110° C. on the treated surfaces. The treated surfaces did not absorb any drop-shaped water at all. The untreated surfaces, on which the contact angle of the water was also very large, i.e. 90-100° C., absorbed water slowly (the sawn surfaces absorbed water faster), which absorption appeared as a clear discolouration of the points on chipboard surface onto which the drops had earlier lain.

In the examples discussed above, the present treatment gave a hydrophobic surface which rejects rain water, reduces water intake of wood panel, and exhibited improved dimensional stability. Still, the surface allows water vapor movements to and from the wood panel. It can be painted with several systems. Importantly it has been found that the surface is less slippery than typically wax coated products. This is important from the point of practical handling of the treated wood products.

Example 4

An aqueous dispersion of AKD having a concentration of 2% was applied onto the surface of spruce plywood by means of a painting roller. The amount of the absorbed dispersion was approximately 0.2 liters/m$^2$. The plywood was dried in a oven at a temperature of 75° C. for a period of 60 minutes at relative humidity of 30%. The contact angle of the water was 115-125° C. on the treated surfaces. The treated surfaces did not absorb any drop-shaped water at all. The untreated surfaces, on which the contact angle of the water was large, i.e. 90 to 100° C., adsorbed water drops within 60 to 120 seconds. The surface of the crosscut end of the spruce plywood absorbed the drops in only 3 to 10 seconds.

While the present invention has been illustrated and described with respect to a particular embodiment thereof, it should be appreciated by those of ordinary skill in the art that various modifications to this invention may be made without departing from the spirit and scope of the present invention.

The invention claimed is:

1. A method of protecting a sawn wood product, comprising the step of applying an aqueous dispersion consisting essentially of alkyl ketene dimer onto an untreated surface of the sawn wood product in order to improve water repellency thereof.

2. The method according to claim 1, wherein water in the aqueous dispersion is vaporized after application.

3. The method according to claim 2, wherein vaporization is carried out at an elevated temperature of approximately 60-130° C.

4. The method according to claim 1, wherein alkyl ketene dimer is applied onto the untreated surface of the sawn wood product in an amount of about 0.5 to 6.5 g/m$^2$.

5. The method according to claim 1, wherein the aqueous dispersion of the alkyl ketene dimer is applied by brushing, spraying, dipping or roller spreading.

6. The method according to claim 1, wherein the aqueous dispersion has an alkyl ketene dimer concentration of about 0.1 to 10% by weight and the aqueous dispersion is applied on the surface of the sawn wood product in an amount of approximately 1 liter per 3-10 square meters of wooden surface.

7. The method according to claim 1, wherein the aqueous dispersion is applied without adjusting the pH value of the surface of the wood.

8. The method according to claim 1, wherein the sawn wood product is one of an unplaned sawn timber, planed sawn timber, beaded-surface wood, sized laminated timber, sized laminated board, pressure impregnated wood, plywood, chipboard, fibre board, veneer based product.

9. The method according to claim 1, wherein the method protects the sawn wood product against the harmful effects of micro organisms.

10. The method according to claim 1, wherein the aqueous dispersion of alkyl ketene dimer is applied onto the untreated surface of the sawn wood product to protect the sawn wood product during a period of outdoor storage.

11. The method according to claim 1, wherein the aqueous dispersion of alkyl ketene dimer is applied on the untreated surface of the sawn wood product such that a non-integral layer of the alkyl ketene dimer is formed on the untreated surface of the sawn wood product.

12. A sawn wood product, consisting essentially of
- a piece of sawn wood having an untreated surface which has not been treated against the harmful effects of microorganisms;
- an alkyl ketene dimer coating on the untreated surface;
- wherein alkyl ketene dimer is deposited on the untreated surface in an amount of 0.5-30 g/m$^2$.

13. The wood product according to claim 12, wherein the sawn wood product is unplaned, planed sawn timber, beaded-surface wood, sized laminated timber, sized laminated board, pressure impregnated wood, plywood products, chipboard, fibre board, laminated veneer lumber or a product made of these materials.

14. The sawn wood product of claim 12, wherein alkyl ketene dimer is deposited on the untreated surface in an amount of 0.5 to 6.5 g/m$^2$.

15. The sawn wood product of claim 12, wherein the sawn wood product is plywood or a veneer based product.

16. The sawn wood product of claim 12, wherein alkyl ketene dimer coating improves dimensional stability; retards wetting; or protects the sawn wood product against the growth of mold or fungi.

17. The method according to claim 6, wherein the aqueous dispersion has an alkyl ketene dimer concentration of about 0.5 to 4% by weight.

18. The method according to claim 6, wherein the aqueous dispersion has an alkyl ketene dimer concentration of about 1.5 to 3% by weight.

19. The method according to claim 1, wherein the aqueous dispersion of alkyl ketene dimer comprises an agent which improves the stability of alkyl ketene dimer.

20. The method according to claim 19, wherein the agent that improves the stability of alkyl ketene dimer is starch.

* * * * *